United States Patent [19]

Maniatis et al.

[11] Patent Number: 4,946,773

[45] Date of Patent: Aug. 7, 1990

[54] DETECTION OF BASE PAIR MISMATCHES USING RNAASE A

[75] Inventors: Thomas P. Maniatis; Richard M. Myers, both of Cambridge, Mass.

[73] Assignee: President and Fellows of Harvard College, Cambridge, Mass.

[21] Appl. No.: 812,261

[22] Filed: Dec. 23, 1985

[51] Int. Cl.$^5$ .................... C12Q 1/68; G01N 33/48; C12N 15/00

[52] U.S. Cl. .................. 435/6; 435/172.3; 435/803; 436/504; 436/63; 436/813; 935/2; 935/4; 935/21; 935/23; 935/78

[58] Field of Search ............ 435/6, 172.3, 803; 436/501, 504, 63, 813; 935/2, 4, 21, 23, 78

[56] References Cited

U.S. PATENT DOCUMENTS 4,395,486 7/1983 Wilson et al. ............... 436/504 X
4,535,058 8/1985 Weinberg et al. .................. 435/6

OTHER PUBLICATIONS

Myers, R. M. et al., "Detection of Single Base Substitutions by Ribonuclease Cleavage . . . ", Science 230, 1242–1246 (13 Dec. 1985).
Winter, E. et al., "A Method to Detect and Characterize Point Mutations . . . .", Proc. Natl. Acad. Sci., U.S.A., 82 (22), 7575–7579 (Nov. 1985).
Langer, P. R. et al., "Enzymatic Synthesis of Biotin-Labeled Polynucleotides . . . ", Proc. Natl. Acad. Sci. 78 (11), 6633–6637 (Nov. 1981).
Orkin et al., Ann. Rev. Genet., vol. 18, p. 131 (1984).
Solomon et al., The Lancet, vol. 1, p. 923 (1979).
Flavell et al., Cell, vol. 15, p. 25 (1978).
Myers et al., Nuc. Acid Res., vol. 13, p. 3111 (1985).
Myers et al., Science, vol. 229, p. 242 (1985).
Wallace et al., Nucl. Acids Res., vol. 6, p. 3543 (1979).
Shenk et al., Proc. Natl. Acad. Sci., U.S.A., vol. 72, p. 989 (1975).
Myers et al., Nuc. Acid. Res., vol. 13, p. 3131 (1985).

Primary Examiner—Esther M. Kepplinger
Assistant Examiner—Richard W. Wagner
Attorney, Agent, or Firm—Fish & Richardson

[57] ABSTRACT

A method for detecting and localizing single base substitutions in RNA or DNA that involves RNAase A cleavage of single base mismatches in RNA:RNA or RNA:DNA heteroduplexes. A RNA probe complementary to wild type DNA is annealed to the test DNA containing a single base substitution. Many of the possible single base mismatches can be cleaved by RNAase A. The location of the single base substitution can be determined by analyzing the sizes of the RNA cleavage products.

14 Claims, 1 Drawing Sheet

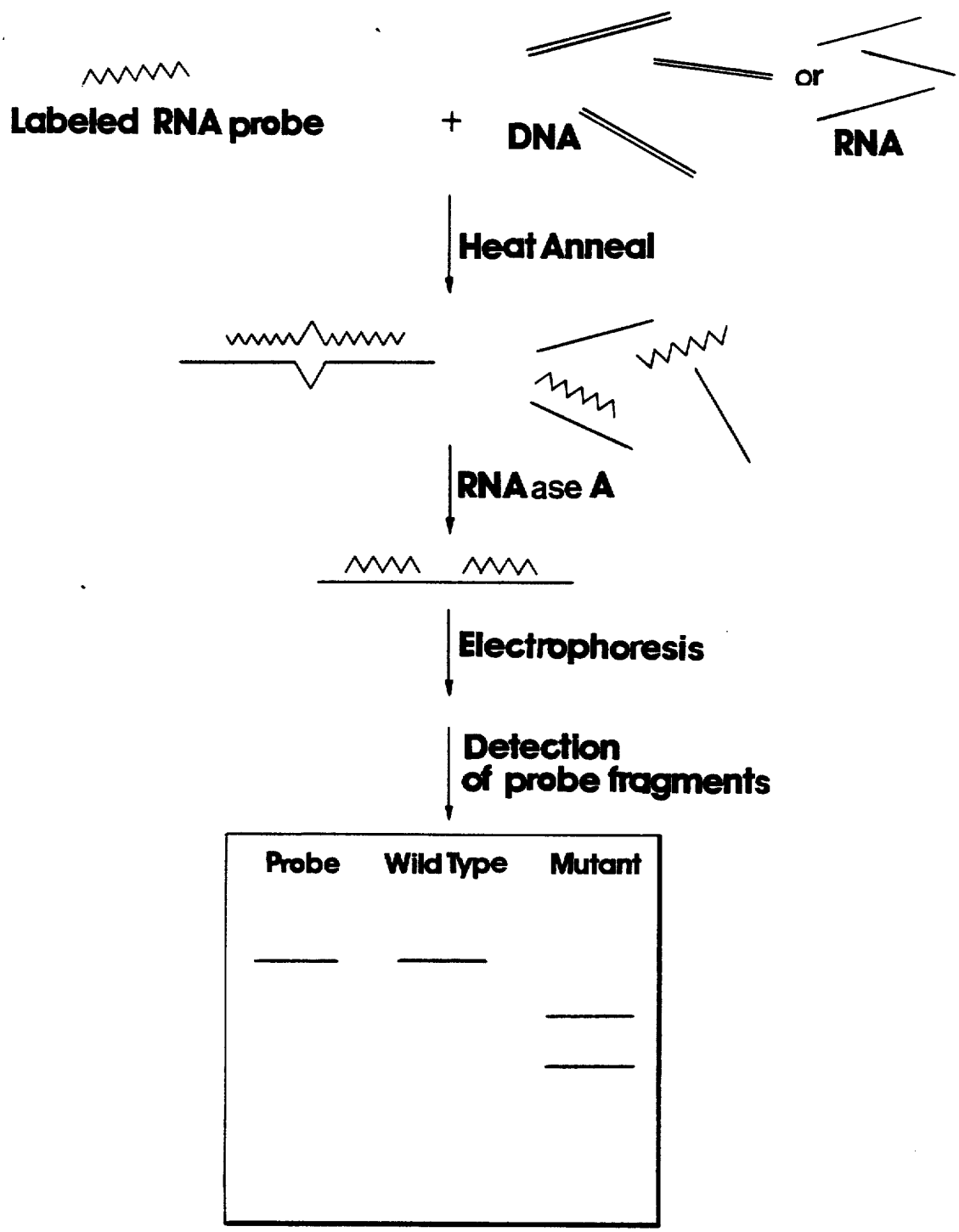

DETECTION OF BASE PAIR MISMATCHES USING RNAASE A

BACKGROUND OF THE INVENTION

This invention relates to a method of detecting mutations in nucleic acid sequences, and pertains more specifically to detection of mutations as small as single base changes.

Methods for detecting single base substitutions in nucleic acids provide powerful tools for the analysis of human genetic diseases (Orkin, et al., 1984 Ann. Rev. Genet. 18:131) and the establishment of human genetic linkage maps (Solomon, et al., 1979 The Lancet 1:923). Procedures currently available for detecting base substitutions rely on differences in restriction endonuclease cleavage sites (Flavell, et al., 1978 Cell 15:25), or on differences in the melting behavior of wild type and mutant DNA duplexes (Myers, et al., 1985 Nuc. Acid Res. 13:3111 and Myers, et al., 1985, Science 229:242). For example, some single base substitutions result in the loss or gain of a restriction endonuclease cleavage site, and can therefore be detected in Southern blotting experiments (Flavell et al., Idem). Another approach involves the use of synthetic oligodeoxyribonucleotides as differential hybridization probes (Wallace, et al., 1979 Nucl. Acids Res. 6:3543). In this method, a labelled synthetic oligonucleotide homologous to the mutant or wild type DNA is hybridized to blotted genomic DNA. Hybridization and washing conditions are then adjusted to allow the differential melting of the mismatched and perfectly paired duplexes. This method is useful for assaying the presence of specific substitutions at known locations.

Another strategy involves detection of mutations in duplex DNA containing single base mismatches (Shenk et al., 1975 Proc. Natl. Acad. Sci. USA 72:989). In this method some DNA:DNA mismatches are cleaved, to a limited extent, with the single strand specific nuclease S1.

SUMMARY OF THE INVENTION

The invention relates to a method for the detection of base pair mismatches between single stranded DNA or RNA samples and a single stranded RNA probe. In general the method involves the annealing together of the single stranded sample and probe, to form a sample duplex, and subsequent treatment with RNAase A. The products of the RNAase A treatment are separated according to size and compared to similarly treated controls consisting of the same RNA probe and a RNA or DNA sample without mismatches (a control duplex). If there is a mismatch between the original sample and the RNA probe the RNAase A treatment will act on the probe and split it into two or more fragments, smaller in size than the original probe. If no mismatch exists between the probe and the sample the probe will remain as a single fragment.

In the preferred embodiment subsequent to RNAase A treatment the products are separated by polyacrylamide or agarose gel electrophoresis. Preferably the RNA probe is labelled either isotopically or non-isotopically, and is used in a greater than ten fold concentration than the sample nucleic acid. The sample and probe may be up to 20 kb in size.

The RNAase A cleavage procedure provides a sensitive, rapid, and simple means of detecting single base substitutions in cloned or genomic DNA. The RNA probes are easily prepared using well-characterized SP6-plasmid vectors, or their equivalent, and the required enzymes are commercially available. In addition, analysis of the sizes of the RNAase A cleavage products of the RNA:DNA or RNA:RNA heteroduplexes not only provides evidence for the presence of a single base mismatch in the test RNA or DNA, but it also makes it possible to localize the mismatch to within a few nucleotides.

The advantages of this method are that many of the possible mismatches in RNA/RNA or RNA/DNA hybrids are specifically cleaved by RNAase A. The RNA probe may be derived from both strands of a DNA fragment and thus more than 50% of all possible base substitutions can be detected. False positives are not generated, so long as a control sample is included in the test, and thus a positive result is unambiguous.

The RNAase A cleavage procedure should be applicable to a variety of problems where the detection and localization of single base substitutions is important. For example, the procedure can be applied to the analysis of human genetic diseases. By establishing sets of SP6-plasmids containing DNA fragments that span an entire gene it should be possible to rapidly survey even the largest genes for single base mutations, the technical limit being near 20 kb. Similarly, this method should be valuable for detecting neutral polymorphisms in genetic linkage studies.

Another potential application of this procedure is the localization of mutations that are selected on the basis of a phenotype. In many genetic systems large numbers of mutants are available for study, but the mutations have not been precisely mapped. The RNAase A cleavage procedure allows rapid localization of many mutations to small DNA fragments that can be detected as single base substitutions. To increase the percentage of mismatches detected this method may readily be combined with physical analytical methods such as denaturing gradient gel electrophoresis (Myers et al., 1985, Nuc. Acid. Res. 13:3131). These two methods complement each other since the basis of detection of mismatches in each differs markedly.

Other features and advantages of the invention will be apparent from the following description of the preferred embodiments and from the claims.

DESCRIPTION OF THE PREFERRED EMBODIMENTS

The figure is a diagrammatic representation of the method of the invention.

The general method of the invention is outlined in the Figure. A RNA probe is synthesized from a DNA template using an in vitro transcription system (Green, et al., 1983, Cell 32, 681-694). This RNA probe is then hybridized to test RNA or denatured test DNA in solution and the resulting RNA:RNA or RNA:DNA hybrid treated with RNAase A. Any non-hybridized RNA will be digested, and the remaining RNA products can then be analyzed by size, preferably by electrophoresis in a denaturing gel. If the test RNA or DNA is identical to the probe RNA a single band is observed in the gel or the autoradiogram of the gel, since the RNA:RNA or RNA:DNA hybrid is not cleaved by RNAase A. However, if the test RNA or DNA contains a single base substitution, and if this mismatch is recognized by RNAase A, two or more new RNA fragments will be detected. The total size of these fragments should equal the size of the original probe RNA. Based on the size of the fragments the mismatch can be localized relative to the ends of the RNA probe. When analyzing a DNA sample the end of the RNA probe mapping nearest to the substitution can be determined by performing the experiment with DNA digested with an additional, different restriction enzyme, thus localizing the substitution unambiguously.

Generally, RNA probes may be derived in vitro from any cloned fragment of DNA. The probe is chosen such that it includes the region of a nucleic acid chain in which it is desired to detect a mutation. The probes are required in a relatively pure state, preferably they are synthesized in vitro from cloned DNA using standard procedures. Preferred are the SP6 and T7 systems which are commercially available from Promega Biotech (Madison, WI), although RNA synthesized from other promoters using different vectors are equally suitable.

Although the RNA need not be labelled it is preferable to do so. One method of labelling involves the synthesis of radioactively labelled RNA by incorporating a radioactively labelled nucleotide during RNA synthesis. Alternatively non-radioactively labelled nucleotides such as biotinylated nucleotides (Langer et al., 1981, Proc. Nat. Acad. Sci. USA 78:6633), may be incorporated. The RNA may also be labelled after its synthesis either radioactively (e.g. by using polynucleotide kinase) or non-radioactively.

RNA probes are preferably full-length so that unambiguous cleavage results may be obtained. That is when RNA probes are synthesized from the appropriate cloned DNA the whole of the cloned DNA is transcribed during the process. With some DNA sequences it is difficult to achieve 100% full-length probe synthesis in the run-off transcription reaction. In these cases, the full-length RNA probe is purified by gel electrophoresis after synthesis.

DNA samples may be derived from cloned or genomic DNA by standard procedures, and need not be purified to homogeneity. Before use the DNA may be digested with a restriction enzyme(s) which does not cleave within the sequence homologous to the RNA probe (although cleavage within the homologous sequence is advantageous if detailed analysis is required at a later time). By performing the annealing and cleavage reactions with this DNA and analyzing the RNA products by gel electrophoresis, the position of a substitution can be mapped accurately relative to one or the other of the two ends of the probe. To determine unambiguously which end of the probe is nearest to the substitution the DNA sample can be digested with a restriction enzyme that cleaves once within the sequence homologous to the probe. After the hybridization reaction, as long as the RNA probe is kept in molar excess, each RNA:DNA duplex will contain a single stranded 'overhang' of RNA probe that will be digested to oligonucleotides in the RNAase A reaction. Analysis of the RNA products by electrophoresis will show a decrease in size of one of the cleavage products when compared to the sample prepared with DNA that was not cleaved within the sequence homologous to the probe, revealing the exact position of the substitution relative to the restriction site.

A RNA sample may be isolated by standard procedures from the cells of interest, for example, somatic cancer cells. The RNA need not be fully purified and does not require denaturing before annealing to the RNA probe.

Standard annealing or hybridization procedures are described by Maniatis et al. (1982 Molecular Cloning: A Laboratory Manual, Cold Spring Harbor Laboratory, N.Y.). Generally they entail two or more single stranded nucleic acids to be mixed together and subjected to conditions in which double strand formation, or hybridization, is favored. For example the mixture may be heated to 90° C. and then gradually cooled to 42° C. in an appropriate buffer.

A time-course of annealing a RNA probe to genomic DNA indicates that hybridization is complete within six hours with 3–6 $\mu$g genomic DNA. Because there may be variations in probe and genomic DNA concentration in different experiments, ten hour hybridizations are recommended to ensure maximum signals. Preferably the probe concentration is ten fold or more greater than that of the sample, most preferably between 10–1000 fold greater.

Any batch of ribonuclease A which is specific for single stranded RNA and can recognize a single base pair mismatch is suitable. Preferably it is obtained from Sigma (Catalog No. R-5125), dissolved in distilled water at a concentration of 2 mg/ml, and placed at 100° C. for 10 minutes. Such a solution may be stored at 4° C. for upwards of one year.

Reaction conditions for RNAase A cleavage are chosen empirically. Buffer containing 100 mM LiCl and 200 mM NaCl suppresses the background to a greater extent than does 300 mM NaCl alone. In addition, a slightly higher temperature (30° C.) of RNAase A treatment results in more complete cleavage of partially cleaved mismatches, but also causes some increase in background. RNAase A treatment at 16° C. in a buffer containing 100 mM LiCl and 100 mM NaCl can also be used.

Some mismatches may only be partially cleaved in the assay. This lack of complete cleavage of some mismatches may pose a difficulty for using the RNAase A cleavage procedure for determining the genotype of a diploid genome. In cases where 50% or less of the RNA probe is cleaved low efficiency of cleavage could be an intrinsic property of the mismatch in question, or the individual may be heterozygous for the mutant allele. This ambiguity may be eliminated in many cases by using a probe of the opposite strand, i.e. a complementary probe, or by performing a time-course of RNAase A treatment. If the mutant allele in question has been cloned, performing the cleavage reaction with RNA probes complementary to this allele may overcome the uncertainty of heterozygosity since the presence of a wild type allele should then be detected in the cleavage products. This approach is especially valuable in the diagnosis of human genetic diseases; in fact, the use of both wild type and mutant oligonucleotide probes is an obligatory requirement of prenatal diagnosis tests (Orkin et al., (1983) J. Clin. Invest. 71:775). Partial cleavage at mismatches is not a problem when examining cloned DNA samples, genomic DNA from haploid organisms, or genomic DNA sequences within the X chromosome of human males. In all of these examples partial cleavage would be diagnostic for the presence of a mutation. In a time-course experiment some mismatches, which are only partially cleaved in 30 minutes, can be cleaved almost to completion in 90 minutes under the same conditions with only a slight increase in background. Thus it is desirable to perform the RNAase A reactions for various lengths of time in cases where partial cleavage occurs.

The temperature and ionic strength of the solution in which the RNAase A reaction is performed contribute significantly to the degree of cleavage and the apparent effects of sequence context. Altering the reaction conditions (i.e. higher temperature and lower ionic strength) results in cleavage at some mismatches that are not normally cleaved and more complete cleavage of mismatches that are normally partially cleaved. These reaction conditions are desirable in some cases but are not ideal since internal cleavage at perfectly matched positions also increases significantly.

Any standard agarose or polyacrylamide gel electrophoresis may be used to separate the RNAase A products by size. The only requirement is that the products of the RNAase A treatment, where a mismatch was present, can be distinguished from the products of such treatment where no mismatches were present.

If the DNA probe is radioactively labelled standard autoradiographic detection procedures may be used to detect the products after electrophoresis. Similarly nonisotopically labelled probes should be readily detected by standard procedures. Unlabelled probes may be visualized after staining the gel with ethidium bromide and exposing it to ultraviolet radiation.

EXAMPLE 1

For convenience, single base mismatches in the RNA:DNA hybrids will be presented as X:Y, where X and Y designate the mismatched RNA and DNA bases, respectively. For example, 'C:A' refers to a mismatch in which cytosine appears in the RNA strand opposite adenine in the DNA strand.

To establish optimal conditions for recognizing single base mismatches, and to determine which types of mismatches can be cleaved by RNAase A, a large number of single base substitutions in the mouse $\beta$-major globin promoter region were examined (Myers et al., 1985, Science 229:242) The RNA probes used in the analysis of the mouse $\beta$-globin promoter are derived from SP6 plasmids containing a 186 bp HinFI to DdeI fragment (from $-106$ to $+72$ relative to the mRNA cap site) of the mouse $\beta$-major globin gene, and radioactively labelled. The sense and antisense probes are obtained by inserting this fragment into pSP64 and pSP65 (Melton et al., 1984, Nucleic Acids Res. 12:7035) in both orientations relative to the bacteriophage promoter. The promoter insert contains eight extra base pairs due to the addition of a BglII linker (sequence 5'CAGATCTG 3') at position $+26$ in the gene. This additional eight bp is also present in the plasmids carrying the mutations.

Uniformly labelled single stranded RNA probes are synthesized with $\alpha$-=P-GTP as the only labelled nucleotide. Bacteriophage SP6 RNA polymerase and $\alpha$-$^{32}$P-labelled GTP are preferably purchased from New England Nuclear; RNAsin from Promega Biotec, and nucleotide triphosphates from PL Biochemicals. Probes used with cloned DNA samples are synthesized with 40 Ci/mmol $\alpha$-$^{32}$P-GTP (at 100 $\mu$M GTP) in the transcription reaction, and can be used for a period of two weeks with little evidence of degradation. Probes used with genomic DNA samples contain 400 Ci/mmol $\alpha$-$^{32}$P-GTP and are used within three days. After synthesis, the probe made from one $\mu$g template DNA is resuspended in 150 $\mu$l 10 mM Tris-HCL, pH 7.5 1 mM EDTA, and 0.1% SDS. Approximately 0.5 $\mu$l probe, which contains $5-10\times10^4$ cpm or $5-10\times10^5$ cpm for probes made for cloned or genomic DNA samples, respectively, is used in each hybridization reaction.

A collection of single base substitutions in the mouse $\beta$-major globin promoter region was generated by a random chemical method followed by purification by denaturing gradient gel electrophoresis (Myers et al. (1985) Science 229:242).

With this collection, it is possible to examine all twelve types of mismatches possible in RNA:DNA hybrids in several different sequence contexts. The RNA probe used in these reactions is 186 nt long, is complementary to the sense strand of the $\beta$-globin promoter (Konkel et al., Idem), and is designated an 'antisense' probe. Annealing to form sample and control duplexes was performed as follows: 20–50 ng of cloned plasmid DNA or 3–6 $\mu$g total genomic DNA in 30 $\mu$l hybridization buffer (80% formamide, 40 mM PIPES, pH 6.4, 0.4 M NaCl, and 1mM EDTA) are added to 0.5 $\mu$l labelled RNA probe and the mixture treated at 90° C. for 10 minutes and then incubated at 45° C. for 30 minutes (cloned DNA) or 10 hours (genomic DNA). After annealing 350 $\mu$l of a solution containing 40 $\mu$g/ml RNAase A in 10 mM Tris-HCL, pH 7.5, 1 mM EDTA, 200 mM NaCl and 100 mM LiCl is added to the hybridization mixture. The sample is then mixed by vortexing and incubated at 25° C. for 30 minutes. The RNAase A reaction is stopped by the addition of 10 $\mu$l 20% SDS and 10 $\mu$l 10 mg/ml proteinase K (Boehringer Mannheim) followed by incubation at 37° C. for 15–30 minutes. Protein is then removed by extraction with an equal volume of phenol:chloroform (1:1) containing 4% isoamyl alcohol and 0.01% hydroxyquinoline. 300 $\mu$l of the aqueous supernatant is carefully removed without disturbing the interface to ensure that no traces of RNAase A remained. After the addition of 10–20 $\mu$g carrier tRNA, the samples are precipitated with ethanol and resuspended in 5 $\mu$l (genomic DNA) or 25 $\mu$l (cloned DNA) loading buffer and analyzed by denaturing polyacrylamide gel electrophoresis. When this probe is annealed to the wild type promoter fragment, to form a control duplex, and then digested with RNAase A a single full-length RNA fragment of 186 nt is observed. In some experiments faint background bands are visible in the wild type lane indicating that a low level of cleavage occurs at bases that are not mismatched. In contrast, when a RNA:DNA sample duplex, containing a C:A mismatch at position $-40$ in the promoter, is analyzed three bands are observed. One of these bands, representing about 50% of the total radioactivity in the lane, corresponds to the full length RNA probe. The lengths of the other two RNA fragments correspond to the sizes expected for cleavage at the mismatch at position $-40$ in the promoter (66 nt and 120 nt). In this and other mismatches examined one of the RNA fragments (the 66 nt fragment) appears as a doublet on the autoradiogram which is probably the result of further reaction of RNAase A at pyrimidines near the ends of the cleaved RNA product. Similar results are obtained with another C:A mismatch located at position $-60$ in the promoter. In contrast, in the case of a third C:A mismatch occurring at $-56$ in the promoter, all of the radioactivity is present in the two cleavage products indicating that 100% of the mismatches are cleaved under the same conditions. Altogether, of twenty-one different C:A mismatches in the promoter tested, greater than 50% of each mismatch is cleaved by RNAase A in every case (see Table 1 below). Similar results are obtained with C:T mismatches (Table 1). In contrast only six of ten U:G mismatches in the promoter are cleaved by RNAase A and the efficiency of cleavage varies from 10% to 90% (Table 1). When the three U:C mismatches are tested, cleavage is very inefficient (only 5% to 10%; Table 1). Three U:T mismatches in the promoter are cleaved at a level of 25% (Table 1).

Several G:G, G:A, G:T, A:A, A:C, and A:G mismatches are formed with mutant promoter DNA fragments and the wild type RNA probes. No cleavage by RNAase A is observed in these mismatches with the following exceptions. A small amount (10% to 20%) of cleavage occurs at two A:A mismatches and one G:T mismatch, and three A:C and two A:G mismatches are cleaved at a high efficiency (Table 1). It is surprising that cleavage occurred at these mismatches since RNAase A cleaves after pyrimidines (Brownlee et al., 1984 Nucl. Acids Res. 12:7035). However it is possible that destabilization of the mismatched RNA:DNA duplex leads to cleavage at nearby pyrimidine bases.

To determine whether this procedure can be used to detect small deletions several promoter fragments containing different single base deletions were analyzed. In each case nearly complete cleavage at the resulting single base 'loop-out', or at nearby pyrimidines, in the probe is observed (Table 1). Similarly, RNA:DNA duplexes containing two mismatches in close proximity are efficiently cleaved in the assay (Table 1).

TABLE 1

Analysis of single base substitution in the mouse β-major globin promoter region and in the human β-globin gene.

| MISMATCH[a] | % CLEAVED[b] | MUTANT[c] | PROBE[d] | CONTEXT[e] |
|---|---|---|---|---|
| C:A | 50 | M −40A | AS | CCCUG |
| | 100 | M −56A | AS | CUCUA |
| | 50 | M −60A | AS | AUCCU |
| | 100 | M −25A | AS | ACCUU |
| | 50 | M −51A | AS | GCCCU |
| | 100 | M −22A | AS | CUCAC |
| | 100 | M −19A | AS | UACCU |
| | 100 | M +19A | AS | AACUA |
| | 50 | M −33A | AS | UGCUC |
| | 50 | M −50A | AS | UGCCC |
| | 100 | M −52A | AS | CCCUC |
| | 100 | M −65T | S | CACAC |
| | 100 | M −63T | S | CACAG |
| | 75 | M −49T | S | GGCAG |
| | 100 | M −42T | S | GCCAG |
| | 50 | M −37T | S | GGCAG |
| | 75 | M −32T | S | AGCAU |
| | 50 | M −4T | S | CUCCU |
| | 100 | M −1T | S | CUCAC |
| | 100 | M +2T | S | CACAU |
| | 60 | M −77T | S | GGCCA |
| | 100 | H Hbe | AS | CUCAC |
| | 50 | H IVS1,1 | AS | AACCU |
| | 100 | H Codon 39 | S | CCCAG |
| C:C | 100 | M −42G | S | GCCAG |
| | 100 | M −32G | S | AGCAU |
| | 100 | M −76G | S | GCCAA |
| | 100 | H IVS1,5C | AS | UACCU |
| C:T | 50 | M −33T | AS | GACCA |
| | 75 | M −25T | AS | AACGU |
| | 75 | M −54T | AS | GACAG |
| | 100 | M −65A | S | CACAC |
| | 100 | M −63A | S | CACAG |
| | 50 | M −43A | S | AGCCA |
| | 100 | M −32A | S | AGCAU |
| | 100 | M −67A | S | CUCAC |
| | 90 | H IVS1,5T | AS | UACCU |
| U:G | 50 | M −57G | AS | UCUAU |
| | 30 | M −31G | AS | UAUGC |
| | 90 | M −26G | AS | CCUUA |
| | 0 | M −48G | AS | CCUGC |
| | 0 | M −45G | AS | GCUCC |
| | 40 | M −59G | AS | UAUCC |
| | 30 | M −34G | AS | CGUCU |
| | 0 | M −23C | S | GGUGA |
| | 10 | M −18C | S | GGUAG |
| | 0 | M +12C | S | UCUGA |
| | 25 | H IVS1,6 | S | GGUAU |
| U:C | 5 | M −62C | AS | CCUGU |
| | 5 | M −66C | AS | UGUGA |
| | 5 | M −45C | AS | GCUCC |
| U:T | 25 | M −13A | S | GAUCA |
| | 25 | M −2A | S | CCUCA |
| | 25 | M +6A | S | UUUGC |
| | 75 | H Sickle | AS | CCUCU |
| G:A | 0 | M −49A | AS | CUGCC |
| | 0 | M −42A | AS | CUGGC |
| | 0 | M −54T | S | GAGAG |
| | 0 | M −35T | S | CAGAG |
| | 0 | M −33T | S | GAGCA |
| | 0 | M −25T | S | AAGGU |

TABLE 1-continued

Analysis of single base substitution in the mouse
β-major globin promoter region and in the human β-globin gene.

| MISMATCH[a] | % CLEAVED[b] | MUTANT[c] | PROBE[d] | CONTEXT[e] |
|---|---|---|---|---|
| | 75 | H IVS1,5T | S | UGGUA |
| G:T | 15 | M −49T | AS | CUGCC |
| | 0 | M −42T | AS | CUGGC |
| | 0 | M −50A | S | GGGCA |
| | 0 | M −51A | S | AGGGC |
| | 0 | M −40A | S | CAGGG |
| | 0 | M −25A | S | AAGGU |
| | 0 | M −22A | S | GUGAG |
| | 0 | M −19A | S | AGGUA |
| | 0 | M −61A | S | CAGGA |
| | 0 | M −60A | S | AGGAU |
| | 0 | M −56A | S | UAGAG |
| | 0 | H Codon 39 | AS | CUGGG |
| | 0 | H IVS1,1 | S | AGGUU |
| | 0 | H Hbe | S | GUGAG |
| G:G | 0 | M −49G | AS | CUGCC |
| | 0 | M −42G | AS | CUGGC |
| | 0 | M −76G | AS | UUGGC |
| | 0 | M −77G | AS | UGGCC |
| | 0 | M +13C | S | CUGAC |
| | 0 | H IVS1,5C | S | UGGUA |
| A:C | 0 | M −23C | AS | UCACC |
| | 0 | M −58C | AS | CUAUC |
| | 75 | M −57G | S | AUAGA |
| | 0 | M −48G | S | GCAGG |
| | 0 | M −74G | S | CAAUC |
| | 0 | M −55G | S | AGAGA |
| | 0 | M −45G | S | GGAGC |
| | 0 | M −34G | S | AGAGC |
| | 100 | M −31G | S | GCAUA |
| | 100 | M −29G | S | AUAUA |
| | 0 | M +14G | S | UGACA |
| | 50 | H IVS1,6 | AS | AUACC |
| A:A | 10 | M −13A | AS | UGAUC |
| | 0 | M −2A | AS | UGAGG |
| | 0 | M −73A | AS | UGAUU |
| | 0 | M −30A | AS | UAAUG |
| | 20 | M −48T | S | GCAGG |
| | 0 | H Sickle | S | UGAGG |
| A:G | 100 | M −66C | S | UCACA |
| | 50 | M −62C | S | UCAGG |
| | 0 | M −45C | S | GGAGC |
| SINGLE | 100 | M +2CD | AS | AUGUG |
| BASE | 100 | M −76CD | AS | UUGGC |
| DELETION | 100 | M +10TD | AS | CUUCU |
| | 100 | M −18TD | AS | GGUAG |
| DOUBLE | 100 | −28G/−26G | AS | |
| MISMATCH | 100 | −28C/−23C | AS | |

Key:
[a]The type of mismatch formed in each case.
[b]The fraction of the total protected RNA probe that is present in cleaved RNA fragments.
[c]The mouse promoter mutants are indicated by M followed by a number designating their position relative to the cap site of β-globin transcription (Lawn et al. (1978) Cell 15:1157). The human β-thalassaemia mutations are indicated by H followed by name of the mutation.
[d]The probe used in each case is designated either as sense (S) or antisense (AS).
[e]The nucleotides surrounding each mismatch in the RNA strand are indicated in a 5' to 3' direction. The underlined nucleotide in each case occurs at the position of the mismatch.

EXAMPLE 2

To establish the feasibility of detecting single base mutations associated with human genetic diseases a number of different cloned and genomic DNAs bearing β-thalassaemia or sickle cell anemia mutations were analyzed. In these experiments the RNA probes used were about 605 bases in length, spanning the region of the gene and 5'—flanking sequences from −128 to +477 (lawn et al. (1978) Cell 15:1157). The RNA probes were derived from plasmids containing a 605 bp RsaI to BamHI fragment of the human β-globin gene.

The plasmids carrying cloned human β-globin genes containing the normal allele or the thalassaemia mutations have been described (Orkin et al. (1984) Ann Rev. Genet. 18:131). A plasmid carrying the sickle allele was made from a bacteriophage λ clone provided by S. Orkin (Orkin et al. 1982 Nature 296:627). Genomic DNA samples from β-thalassaemia patients were used (Orkin et al. Idem.). Two separate RNA probes were synthesized so that both the sense and antisense strand of the region could be tested. With this set of substitutions and probes ten of the twelve types of RNA:DNA mismatches could be formed and seven out of the ten types are cleaved to some extent by RNAase A (Table 1).

To determine whether the RNAase A cleavage procedure could be used to detect single base substitutions in total genomic DNA, DNA samples from two individuals with β-thalassaemia were analyzed. One individual carried a C to T transition at codon 39 of the β-globin gene in both chromosomes. The second individual was homozygous for the HbE allele, which contains a G to A transition at codon 26 in the gene. The codon 39 DNA was tested with the sense strand RNA probe, whereas the HbE DNA was tested with the antisense RNA probe. Both of these hybrids result in C:A mismatches with their corresponding probes. When the experiment is performed with the sense probe and genomic DNA from an individual with wild type β-globin genes a single band appearing at the full-length position results. When DNA from the individual homozygous for the codon 39 mutation is analyzed RNA fragments 430 and 185 nt in length are observed, indicating that cleavage at the C:A mismatch occurred at a high efficiency. Similar results are obtained with the analogous cloned DNA samples. In another experiment, using the antisense RNA probe, genomic DNA from an individual with normal β-globin genes also results in a single band appearing at the full-length probe position. Genomic DNA from a patient homozygous for the HbE allele results in two RNA fragments of the expected sizes of 355 nt and 260 nt, again indicating complete cleavage of the mismatch by RNAase A. These results are obtained by using 3 μg of total genomic DNA and RNA probes with a specific activity of 400 Ci/mmol $\alpha^{32}$ P-GTP. A signal can be clearly detected after a 24 hour autoradiographic exposure. These experiments establish the feasibility of using the RNAase method to detect single base mutations and linked polymorphisms in genomic DNA at a level of sensitivity at least comparable with existing techniques.

Examination of the data summarized in Table 1 indicates that four out of the twelve possible types of mismatches (C:A, C:C, C:T, and U:T) are recognized efficiently by RNAase A in all sequence contexts tested. Thus approximately one-third of all possible single base substitutions can be detected using an RNA probe homologous to one strand of the test DNA. This number can be doubled by using a second RNA probe homologous to the opposite strand of the test DNA. For example, a G:T mismatch formed between one strand of the test DNA and the homologous RNA probe may not be cleaved by RNAase A. When the other DNA strand is hybridized to its homologous RNA probe the C:A mismatch at that same position will be cleaved by RNAase A. Thus approximately two-thirds of all possible single base substitutions can be detected. This is clearly a minimum estimate since cleavage at seven of the remaining eight possible types of mismatches was observed in some sequence contexts.

Other embodiments are within the following claims.

We claim:

1. A method to detect at least one single base pair mismatch between a single stranded DNA or RNA sample and a single stranded RNA probe wherein said method comprises:
    annealing together said single stranded DNA or RNA sample and said single stranded RNA probe to form a sample duplex,
    providing a control duplex comprising said single stranded RNA probe and a polynucleotide strand, wherein said duplex is free from mismatches,
    mixing said sample duplex and said control duplex with RNAase A,
    separating by size the products of said RNAase A treatment,
    and comparing the number and sizes of the products from said sample duplex with the products from identically treated said control duplex, as an indication of the presence or absence of a mismatch in said sample duplex.

2. The method of claim 1 wherein said separation is by gel electrophoresis.

3. The method of claim 2 wherein said electrophoresis is through agarose or polyacrylamide.

4. The method of claim 1 wherein said single stranded RNA probe is labelled.

5. The method of claim 4 wherein said label is radioactive or nonradioactive.

6. The method of claim 5 wherein said non-isotopic label is biotin.

7. The method of claim 1 wherein said method detects a single base deletion in said sample.

8. The method of claim 1 wherein said single stranded RNA probe is present at 10 fold or greater excess in comparison to said single stranded DNA or RNA sample.

9. The method of claim 8 wherein said excess is between 10 fold to 1,000 fold.

10. The method of claim 1 wherein said single stranded RNA probe is synthesized from an SP6 or T7 promoter.

11. The method of claim 1 wherein said single stranded RNA probe is less than 20 kb in size.

12. The method of claim 1 wherein said single stranded sample is less than 20 kb in size.

13. The method of claim 1 wherein said single stranded sample is derived from genomic DNA.

14. The method of claim 1 wherein said RNA sample is derived from somatic cells.

* * * * *

UNITED STATES PATENT AND TRADEMARK OFFICE
CERTIFICATE OF CORRECTION

PATENT NO. : 4,946,773

DATED : August 7, 1990

INVENTOR(S) : Thomas P. Maniatis et al.

It is certified that error appears in the above-identified patent and that said Letters Patent is hereby corrected as shown below:

Column 5, line 20, "DNA" should be --RNA--;

Column 5, line 54, "$\alpha - = P\text{-}GTP$" should be --$\alpha - {}^{32}P\text{-}GTP$--;

Column 12, line 28, "non-isotopic" should be --nonradioactive--; and add --FIGURE-- label to drawing.

Signed and Sealed this

Twenty-fifth Day of August, 1992

Attest:

DOUGLAS B. COMER

Attesting Officer    Acting Commissioner of Patents and Trademarks

UNITED STATES PATENT AND TRADEMARK OFFICE
CERTIFICATE OF CORRECTION

PATENT NO. : 4,946,773

DATED : August 7, 1990

INVENTOR(S) : Thomas P. Maniatis and Richard M. Myers

It is certified that error appears in the above-identified patent and that said Letters Patent is hereby corrected as shown below:

Column 1, line 6:

--This invention was made with government support under Grant No. HL 27898 awarded by the National Institutes of Health. The government has certain rights in the invention.--

Signed and Sealed this

First Day of August, 1995

Attest:

BRUCE LEHMAN

*Attesting Officer*  *Commissioner of Patents and Trademarks*